US010716740B2

(12) United States Patent
Sunkel et al.

(10) Patent No.: US 10,716,740 B2
(45) Date of Patent: *Jul. 21, 2020

(54) FOAM COMPOSITIONS, AEROSOL PRODUCTS, AND METHODS OF USING THE SAME TO IMPROVE SENSORY BENEFITS TO THE SKIN

(71) Applicant: The Procter & Gamble Company, Cincinnati, OH (US)

(72) Inventors: Jorge Max Sunkel, Cincinnati, OH (US); Dean Arthur Zimmerman, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 172 days.

This patent is subject to a terminal disclaimer.

(21) Appl. No.: 15/073,725

(22) Filed: Mar. 18, 2016

(65) Prior Publication Data

US 2016/0279035 A1    Sep. 29, 2016

Related U.S. Application Data

(60) Provisional application No. 62/137,299, filed on Mar. 24, 2015.

(51) Int. Cl.
| | | |
|---|---|---|
| *A61K 8/34* | (2006.01) | |
| *A61K 8/89* | (2006.01) | |
| *A61K 8/04* | (2006.01) | |
| *A61K 8/19* | (2006.01) | |
| *A61K 8/41* | (2006.01) | |

(Continued)

(52) U.S. Cl.
CPC .............. *A61K 8/046* (2013.01); *A61K 8/19* (2013.01); *A61K 8/342* (2013.01); *A61K 8/416* (2013.01); *A61K 8/89* (2013.01); *A61K 8/891* (2013.01); *A61Q 19/00* (2013.01);
(Continued)

(58) Field of Classification Search
CPC .......... A61K 8/04; A61K 8/046; A61K 8/342; A61K 8/25; A61K 8/89; A61K 8/891; A61K 8/892; A61K 8/895; A61K 8/416
See application file for complete search history.

(56) References Cited

U.S. PATENT DOCUMENTS

| | | | |
|---|---|---|---|
| 3,970,584 A | 7/1976 | Hart | |
| 6,264,964 B1 | 7/2001 | Mohammadi | |

(Continued)

FOREIGN PATENT DOCUMENTS

| | | |
|---|---|---|
| EP | 1555983 | 10/2010 |
| EP | 2191811 | 11/2013 |

(Continued)

OTHER PUBLICATIONS

Whipped Shimmer Body Cream Record ID# 2207948; Bath & Body Works; Oct. 2013; www.gnpd.com.

(Continued)

*Primary Examiner* — Lakshmi S Channavajjala
(74) *Attorney, Agent, or Firm* — Alexandra S. Anoff

(57) ABSTRACT

A liquid foamable composition includes a cationic surfactant, a nonionic surfactant, or mixtures of these surfactants, a fatty alcohol, a silicone blend, and water. The silicone blend includes a silicone gel and a silicone powder. A foam composition, an aerosol product, and methods for improving sensory benefits to skin are also provided.

34 Claims, 3 Drawing Sheets

(51) Int. Cl.
*A61K 8/891* (2006.01)
*A61Q 19/00* (2006.01)

(52) U.S. Cl.
CPC .... *A61K 2800/30* (2013.01); *A61K 2800/546* (2013.01); *A61K 2800/594* (2013.01); *A61K 2800/87* (2013.01)

(56) References Cited

U.S. PATENT DOCUMENTS

| | | | |
|---|---|---|---|
| 7,029,659 | B2 | 4/2006 | Abram |
| 8,852,563 | B2* | 10/2014 | Kasagi ............ A61K 8/0241 |
| | | | 424/59 |
| 2002/0045670 | A1 | 4/2002 | Lorant |
| 2003/0118515 | A1 | 6/2003 | Jew |
| 2004/0184992 | A1 | 9/2004 | Abram |
| 2004/0258628 | A1 | 12/2004 | Riedel |
| 2005/0205086 | A1 | 9/2005 | Tamarkin |
| 2005/0222001 | A1* | 10/2005 | Baumeister ......... A61K 8/046 |
| | | | 510/123 |
| 2006/0034792 | A1 | 2/2006 | Lazzeri |
| 2006/0233721 | A1 | 10/2006 | Tamarkin |
| 2006/0292080 | A1 | 12/2006 | Abram |
| 2007/0160636 | A1 | 7/2007 | Kasai |
| 2008/0031907 | A1* | 2/2008 | Tamarkin ............ A61K 8/046 |
| | | | 424/401 |
| 2008/0044444 | A1 | 2/2008 | Tamarkin |
| 2008/0131378 | A1 | 6/2008 | Keller |
| 2008/0138296 | A1 | 6/2008 | Tamarkin |
| 2008/0139453 | A1* | 6/2008 | Yoshimi ............. A61K 8/066 |
| | | | 424/59 |
| 2012/0288465 | A1 | 11/2012 | Loechel |
| 2013/0183250 | A1 | 7/2013 | Tamarkin |
| 2013/0295022 | A1 | 11/2013 | Tamarkin |
| 2014/0086848 | A1 | 3/2014 | Tamarkin |
| 2014/0120039 | A1 | 5/2014 | Graham |

FOREIGN PATENT DOCUMENTS

| | | |
|---|---|---|
| WO | WO2004037225 | 5/2004 |
| WO | WO2012160169 | 11/2012 |

OTHER PUBLICATIONS

Sunblock Mousse SPF 50 PA+++ Record ID# 2307289; Nobile; Feb. 2014 www.gnpd.com.

Anti-Wrinkle Firming Moisturiser Record ID# 632836; RoC; Dec. 2006 www.gnpd.com.

* cited by examiner

FOAM COMPOSITIONS, AEROSOL PRODUCTS, AND METHODS OF USING THE SAME TO IMPROVE SENSORY BENEFITS TO THE SKIN

TECHNICAL FIELD

The present disclosure generally relates to foam compositions, aerosol products, and methods of using the same to improve sensory benefits to the skin of a consumer.

BACKGROUND

There are many types of skin care products that are commercially available or otherwise known in the art, and there are many factors that can contribute to the purchase intent of a consumer when looking for such products. Critical among these factors are the sensory benefits that the skin care product can provide. As such, there is a consistent desire to develop new ways to deliver a positive sensory experience to consumers.

Skin care products have often employed polymers as a way to manage rheological properties to promote performance benefits. However, some of these polymers are not optimized to provide the desired sensory benefits. For example, elevated polymer concentrations, relative to evaporating fluids, can thicken fluids that remain on the skin during product application and subsequent dry-down, resulting in tack, drag, stickiness, or other negative sensory aspects. Further, such negative aspects can continue after the dry-down phase as a result of sweating and humidity fluctuations.

Using a foam composition is one way to reduce or eliminate the use of polymers. For example, foams can use air to thicken a product in place of polymers. Thus, foams can convey a desired rich and creamy aesthetic while reducing or eliminating the negative sensory aspects associated with the use of polymers. Further, foams can easily absorb into the skin as they can rapidly break down into fluids. However, certain foam compositions can lack the stability that may otherwise be provided by skin care products with polymers. Application of foams lacking the necessary stability can also result in a negative sensory experience for a consumer.

Therefore, what is desired is a skin care product in the form of a foam composition, which possesses robust stability and an ability to provide desired sensory benefits.

SUMMARY

In accordance with one example, a liquid foamable composition includes from about 0.05% to about 5%, by weight, of a surfactant selected from the group consisting of a cationic surfactant, a non-ionic surfactant and mixtures thereof, from about 1% to about 10%, by weight, of a fatty alcohol, from about 10% to about 50%, by weight, of a silicone blend, and the remainder is water. The silicone blend includes a first silicone component having a silicone gel and a second silicone component having a silicone powder.

In accordance with another example, a foam composition is formed from combining a liquid foamable composition with a propellant. The liquid foamable composition includes from about 0.05% to about 5%, by weight, of a cationic surfactant, a surfactant selected from the group consisting of a cationic surfactant, a non-ionic surfactant and mixtures thereof, from about 1% to about 10%, by weight, of a fatty alcohol, from about 10% to about 50%, by weight, of a silicone blend, and the remainder is water. The foam composition exhibits a foam density of about 0.1 g/mL to about 0.5 g/mL. The initial liquid composition typically has a density of from about 0.9 g/mL to about 1.1 g/mL, and the density decreases as the liquid turns to foam.

In accordance with yet another example, an aerosol product includes a liquid foamable composition, a propellant, and a package. The liquid foamable composition includes from about 0.05% to about 5%, by weight, of a surfactant selected from the group consisting of a cationic surfactant, a non-ionic surfactant and mixtures thereof, from about 1% to about 10%, by weight, of a fatty alcohol, from about 12% to about 30%, by weight, of a silicone blend, and the remainder is water. The silicone blend includes a first silicone component having a silicone gel and a second silicone component having a silicone powder. The package houses the liquid foamable composition and the propellant. The liquid foamable composition and the propellant are dispensable from the package as a foam, wherein such foam exhibits a foam density of about 0.1 g/mL to about 0.5 g/mL.

In accordance with still another example, a method for improving sensory benefits to skin includes applying a foam composition to the skin of a user. The foam composition includes a liquid foamable composition and a propellant. The liquid foamable composition includes from about 0.05% to about 5%, by weight, of a surfactant selected from the group consisting of a cationic surfactant, a non-ionic surfactant and mixtures thereof, from about 1% to about 10%, by weight, of a fatty alcohol, from about 10% to about 50%, by weight, of a silicone blend, and the remainder is water. The silicone blend includes a first silicone component having a silicone gel and a second silicone component having a silicone powder.

DETAILED DESCRIPTION

I. Definitions

Figure 1:
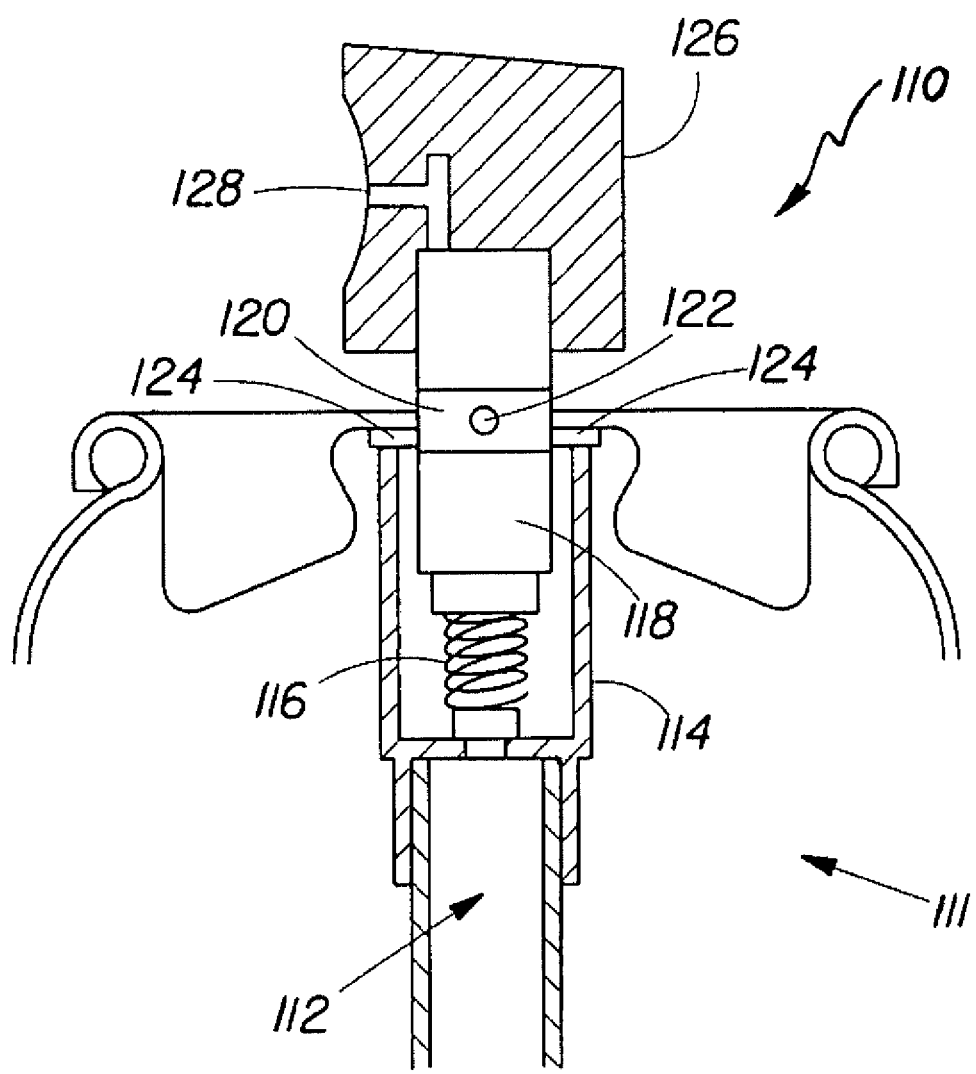
FIG. 1 depicts a side elevational view in partial section of an assembled valve mounted to a container according to one example.

As used herein, the following terms shall have the meaning specified thereafter:

"Non-volatile," as it relates to at least fatty alcohols and silicones, can refer to having a boiling point at 1.0 atmospheres of about 260° C. or greater, about 275° C. or greater, or about 300° C. or greater.

"Polymer" can refer to materials formed by polymerization of one type of monomer or formed by polymerization of two or more types of monomers (i.e., copolymers).

"Water soluble" can refer to being sufficiently soluble in water to form a solution that is substantially clear to a naked eye at a concentration of 0.1% in water (distilled or equivalent) at 25° C. The polymer can be sufficiently soluble to form a substantially clear solution at 0.5% concentration in water, and likely to form a substantially clear solution at 1.0% concentration in water.

II. Foam Compositions

Surprisingly, it was found that, due to the use of an effective amount of a particular silicone blend, a very rich and creamy foam composition with robust stability and an ability to provide desired sensory benefits can be achieved. The foam composition can be formed from the combination of a liquid foamable composition with a propellant. A liquid composition is generally foamable if it has the ability to entrain or entrap gas (e.g., carbon dioxide). The liquid foamable composition, can be based on a combination of a cationic surfactant (e.g., typically a quaternary ammonium compound), a non-ionic surfactant, a fatty alcohol, and a silicone blend.

Further, it has been found that a foam composition can exhibit a robust foam density. As shown below, in Table 2 in the Examples, inventive examples of a foam composition (i.e., Inventive Examples A-E) outperformed comparative examples (i.e., Comparative Examples A-C). In certain examples, the foam composition can exhibit a foam density from about 0.1 g/mL to about 0.5 g/mL, and in certain examples from about 0.12 g/mL to about 0.4 g/mL. Foam density of the foam composition can be determined according to the Foam Density Determination Method described herein.

Essential ingredients, as well as a non-exclusive list of optional ingredients, are described below.

A. Liquid Foamable Composition

A liquid foamable composition can include a cationic surfactant (e.g., typically a quaternary ammonium compound), a non-ionic surfactant, a fatty alcohol, a silicone blend, water, and other optional ingredients (e.g., skin care actives, glycerin, a super-absorbent polymer). Specific types and ranges for these components are described herein.

Cationic Surfactants

Cationic surfactants suitable for use in the liquid foamable composition can include amino or quaternary ammonium moieties. Additional suitable cationic surfactants are disclosed in the following documents, all incorporated by reference herein: M.C. Publishing Co., McCutcheon's, Detergents & Emulsifiers, (North American edition 1979); Schwartz, et al., Surface Active Agents, Their Chemistry and Technology, New York, Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983. Suitable quaternary ammonium compounds can include those of the general formula:

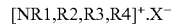

$[NR_1,R_2,R_3,R_4]^+ \cdot X^-$ wherein R1 to R4 can independently be an aliphatic group of from about 1 to about 22 carbon atoms or an aromatic, alkoxy, polyoxyalkylene, alkylamido, hydroxyalkyl, aryl, or alkylaryl group having from about 1 to about 22 carbon atoms; and $X^-$ can be a salt-forming anion, such as those selected from halogen (e.g., chloride, bromide, iodide), acetate, citrate, lactate, glycolate, phosphate nitrate, sulfate, and alkylsulfate radicals.

Such aliphatic groups can contain, in addition to carbon and hydrogen atoms, either linkages or other groups, such as amino groups. The longer-chain aliphatic groups (e.g., those of about 12 carbons, or higher) can be saturated or unsaturated. Mono-long alkyl quaternized ammonium salt cationic surfactants can include behenyl trimethyl ammonium salt, stearyl trimethyl ammonium salt, cetyl trimethyl ammonium salt, and hydrogenated tallow alkyl trimethyl ammonium salt. Di-long chain (e.g., di $C_{12}$-$C_{22}$, $C_{16}$-$C_{18}$, aliphatic, alkyl) and di-short chain (e.g., $C_1$-$C_3$ alkyl, $C_1$-$C_2$ alkyl) ammonium salts can also be employed. Other suitable quaternary ammonium salt useful as cationic surfactants are described in U.S. Pat. No. 8,936,798, which is hereby incorporated by reference.

Salts of primary, secondary, and tertiary fatty amines can also be suitable cationic surfactant materials. The alkyl groups of such amines can have from about 12 to about 22 carbon atoms, and may be substituted or unsubstituted. Such amines can include stearamidopropyl dimethylamine, behenylamidopropyl dimethylamine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts can include halogen, acetate, phosphate, nitrate, citrate, lactate, and alkyl sulfate salts. Such salts can include stearylamine hydrochloride, soyamine chloride, stearylamine formate, N-tallowpropane diamine dichloride, and stearamidopropyl dimethylamine citrate. Suitable cationic amine surfactants for the liquid foamable composition are disclosed in U.S. Pat. No. 4,275,055, Nachtigal, et al., issued Jun. 23, 1981, incorporated by reference herein. In certain examples, suitable cationic surfactants can include behenyl trimethyl ammonium chloride, stearyl ethylhexyldimonium methosulfate, dicetyldimonium chloride, ditallow dimethyl ammonium chloride, GENAMIN® CTAC (i.e., cetyl trimethyl ammonium chloride), esterquats (e.g., tetradecyl betainester chloride), diesterquats (e.g., dipalmitylethyl dimethyl ammonium chloride, ARMOCARE® VGH70 of Akzo, Germany), or a mixture of distearoylethyl hydroxyethylmonium methosulfate and Cetearyl Alcohol (DEHYQUART® F-75 of Henkel, Germany).

In certain examples, cationic surfactants (e.g., quaternary ammonium compounds) can be included at concentration levels from about 0.05% to about 5%, by weight, of the liquid foamable composition, and in certain examples, from about 1% to about 4%, by weight of the liquid foamable composition. Quaternary ammonium compounds may comprise one or more of behenyl trimethyl ammonium chloride, stearamidopropyl dimethylamine, behentrimonium methosulfate ("BTMS"), behenylamidopropyl dimethylamine, stearyl ethylhexyldimonium methosulfate, dicetyldimonium chloride, and ditallow dimethyl ammonium chloride.

Nonionic Surfactants

Surfactants useful in the present invention may also be selected from nonionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula RCO(X)$_n$OOCR wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula R(X)$_n$OR' wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula RCO(X)$_n$OR' wherein R and R' are C10-30 alkyl groups, X is —OCH$_2$CH$_2$ (i.e. derived from ethylene glycol or oxide) or —OCH$_2$CHCH$_3$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

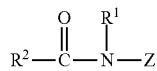

wherein: R$^1$ is H, C$_1$-C$_4$ alkyl, 2-hydroxyethyl, 2-hydroxypropyl, preferably C$_1$-C$_4$ alkyl, more preferably methyl or ethyl, most preferably methyl; R$^2$ is C$_5$-C$_{31}$ alkyl or alkenyl, preferably C$_7$-C$_{19}$ alkyl or alkenyl, more preferably C$_9$-C$_{17}$ alkyl or alkenyl, most preferably C$_{11}$-C$_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R$^2$CO— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety. Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Fatty Alcohols

A liquid foamable composition can include a fatty alcohol. For example, the liquid foamable composition can include monohydric saturated straight-chain fatty alcohols, such as one or more of behenyl alcohol, cetyl alcohol, and stearyl alcohol, and other waxy fatty alcohols having melting points of about 25° C. or higher, or of about 45° C. or higher; and at levels of about 10% or less, by weight of the liquid foamable composition; and about 4% or less, by weight of the liquid foamable composition.

In certain examples, the fatty alcohols can be non-volatile and have a low melting point. For example, such fatty alcohols can have a melting point of 30° C. or less, about 25° C. or less, or about 22° C. or less. Unsaturated fatty alcohols can also be non-volatile. Suitable fatty alcohols can include unsaturated monohydric straight-chain fatty alcohols, saturated branched-chain fatty alcohols, saturated C$_8$-C$_{12}$ straight-chain fatty alcohols, and mixtures thereof. The unsaturated straight-chain fatty alcohols can typically have one degree of unsaturation. Di- and tri-unsaturated alkenyl chains can be present at low levels; about 5% or less, by total weight of the unsaturated straight-chain fatty alcohol; about 2% or less, by total weight of the unsaturated straight-chain fatty alcohol; and about 1% or less, by total weight of the unsaturated straight-chain fatty alcohol. The unsaturated straight-chain fatty alcohols can have an aliphatic chain size of from C$_{12}$-C$_{22}$ in certain examples, from C$_{12}$-C$_{18}$ in certain examples, and from C$_{16}$-C$_{18}$ in certain examples. Exemplary alcohols of this type can include oleyl alcohol and palmitoleic alcohol.

Branched-chain alcohols can typically have aliphatic chain sizes of from C$_{12}$-C$_{22}$, C$_{14}$-C$_{20}$ in certain examples, and C$_{16}$-C$_{18}$ in certain examples. Suitable branched-chain alcohols can include isostearyl alcohol, octyl dodecanol, and octyl decanol.

Examples of saturated C$_8$-C$_{12}$ straight-chain alcohols can include octyl alcohol, caprylic alcohol, decyl alcohol, and lauryl alcohol. Fatty alcohols having a low melting point can be included at levels from about 0.1% to about 10%, by weight of the liquid foamable composition, from about 0.2% to about 5%, by weight of the liquid foamable composition in certain examples; and from about 0.5% to about 3%, by weight of the liquid foamable composition in certain examples.

It may be desirable to use waxy fatty alcohols for their conditioning benefits. However, if both waxy fatty alcohols and liquid fatty alcohols are present, a weight ratio of liquid to waxy fatty alcohols can be about 0.25 or less, in certain examples; about 0.15 or less, in certain examples; and about 0.10 or less, in certain examples.

A total amount of fatty alcohols in the liquid foamable composition can be from about 1% to about 10%, by weight; from about 2% to about 8%, by weight; and from about 3% to about 6%, by weight. In certain examples, a ratio of the fatty alcohol to the cationic surfactant can be about 2 parts to about 1 part. In such examples, the fatty alcohol and the cationic surfactant can combine to form liquid crystal structures in a lamellar gel phase. In examples where the ratio of the fatty alcohol to the cationic surfactant is lower (i.e., an amount of cationic surfactant is increased relative to an amount of fatty alcohol), the liquid crystal structures can be in the form of vesicles. In certain examples, the liquid crystal structures can be of any of a variety of suitable phases including, for example, bicontinuous cubic, hexagonal, inverse cubic, micellar cubic, reverse hexagonal columnar, and combinations thereof. Examples of liquid crystal structures are further described in U.S. Pat. No. 8,470,305 and PCT International Publication No. WO 2010/060131, both of which are hereby incorporated by reference.

Silicone Blend

The liquid foamable composition can include from about 10% to about 50%, by weight; from about 12% to about 30%, by weight; from about 14% to about 25%, by weight; or from about 15% to about 20%, by weight, of a silicone blend. The silicone blend can include two or more silicone components. For example, the silicone blend can include a silicone gel and a silicone powder. In certain examples, the silicone gel can include a silicone fluid.

The silicone blend can include from about 75% to about 85%, by weight, of a silicone gel (e.g., DC 9040 and DC 9045, made by DOW CORNING® KSG-15, KSG-16, and KSG-16F made by SHIN-ETSU®; VELVESIL® 125, VELVESIL® DM, and SFE839 made by MOMENTIVE®). In certain examples, the silicone gel can include a silicone fluid (e.g., cyclomethicone D5 and D6, and dimethicone fluids). A silicone fluid can refer to flowable silicone materials having a viscosity of 1,000,000 centistokes or less at 25° C. Generally, the viscosity can be between about 1 centistoke and 1,000,000 centistokes at 25° C., and likely between about 2 centistokes and about 300,000 centistokes at 25° C. In certain examples, the silicone gels can be crosslinked silicone elastomers.

The silicone blend can further include from about 15% to about 25%, by weight; and about 18%, by weight, of a silicone powder (e.g., KSP-100, KSP-102, KSP-105 and other powders from SHIN-ETSU®; DC 9506, DC 9701, etc. from DOW CORNING®/TORAY®; and TOSPEARL® from MOMENTIVE®). As such, a ratio of the silicone gel to the silicone powder can be about 3 parts to about 1 part in certain examples. The silicone powders can also be crosslinked silicone elastomers. In certain examples, the silicone powders can be crosslinked to a greater degree than the silicone gels. Such silicone powders can absorb less fluids, per unit weight of polymer, than the silicone gels, and the silicone powders can generally be harder (i.e., less compressible) than silicone gels. In certain examples, the silicone powders can be supplied as 100% powder (i.e., without any fluid). Silicone powders can take the form of substantially spherical particles or be amorphous in shape.

The silicone blend can optionally include from about 0.05% to about 4%, by weight; and about 2%, by weight, of a wetting agent (e.g., SF 1288® and others from the SILWET®/SILSOFT® line of wetting agents from MOMENTIVE®).

The liquid foamable composition can also include non-volatile soluble or insoluble silicone conditioning agents. A soluble silicone conditioning agent can be miscible with an aqueous carrier to form part of the same phase. An insoluble silicone conditioning agent can be a silicone from a separate, discontinuous phase from the aqueous carrier, such as in the form of an emulsion or a suspension of droplets of the silicone.

Soluble silicones can include silicone copolyols, such as dimethicone copolyols, and polyether siloxane-modified polymers, such as polypropylene oxide and polyethylene oxide modified polydimethylsiloxane, wherein the level of ethylene and/or propylene oxide can be sufficient to allow solubility in the liquid foamable composition.

Insoluble silicone conditioning agent can have a viscosity of from about 1,000 centistokes to about 2,000,000 centistokes at 25° C. in certain examples, from about 10,000 centistokes to about 1,800,000 centistokes in certain examples, and from about 100,000 centistokes to about 1,500,000 centistokes at 25° C. in certain examples. The viscosity can be measured by means of a glass capillary viscometer as set forth in Dow Corning Corporate Test Method CTM0004, Jul. 20, 1970. Suitable insoluble silicones can include polyalkylsiloxanes, polyarylsiloxanes, polyalkylarylsiloxanes, polyethersiloxane copolymers, and mixtures thereof, each of which are described in U.S. Pat. No. 8,017,106, which is incorporated by reference herein.

Other Components

The liquid foamable composition can include water in amount such that water can provide a remainder of the liquid foamable composition. As such, a liquid foamable composition can include from about 50% to about 98%, by weight; from about 50% to about 80%, by weight; or from about 70% to about 75%, by weight, of water.

In certain examples, the water may include other liquid, water-miscible, or water-soluble solvents such as lower alkyl alcohols (e.g., $C_1$-$C_5$ alkyl monohydric alcohols), such as $C_2$-$C_3$ alkyl alcohols. However, the liquid fatty alcohol must be miscible in an aqueous portion of the liquid foamable composition. The fatty alcohol can be naturally miscible in the aqueous portion or can be made miscible through the use of co-solvents or surfactants.

The liquid foamable composition can also include a variety of other optional components suitable for rendering such compositions more cosmetically or aesthetically acceptable or to provide them with additional usage benefits. Such conventional optional ingredients can be well-known to those skilled in the art.

For example, the liquid foamable composition can also include one or more additional conditioning agents, such as those selected from the group consisting of avocado oil, fatty acids, hexyldecanol, isopropyl myristate, lanolin, apple wax, bees wax or jojoba oil, phospholipids (e.g., lecithines or ceramides), vaseline non-volatile hydrocarbons, and hydrocarbon esters. Imidazolidinyl derivatives, such as INCI Quaternium-87 (REWOQUAT® W 575 of Witco, Germany) can also be useful.

In certain examples, the liquid foamable composition can include a superabsorbent polymer. Suitable superabsorbent polymers can include polyacrylates (e.g., sodium polyacrylate starch) and polyacrylic acid polymers. Suitable materials are described, for example, in PCT Patent Applications WO 07/047598, WO 07/046052, WO2009/155265 and WO2009/155264, all of which are hereby incorporated by reference. In certain examples, suitable superabsorbent polymer particles can be obtained by current state-of-the-art production processes, such as those described in WO 2006/083584, which is hereby incorporated by reference. The superabsorbent polymers can be internally cross-linked (i.e., polymerization can be carried out in the presence of compounds having two or more polymerizable groups that can be free-radically copolymerized into the polymer network), externally surface crosslinked, or post crosslinked. Additional suitable superabsorbent polymers are described in U.S. Patent Publication No. 2013/0243836 and PCT International Application No. PCT/US2013/032922, each of which is hereby incorporated by reference.

A wide variety of additional ingredients can be included within the liquid foamable composition. Such ingredients can include other conditioning agents (e.g., betaine, carnitin esters, creatine, amino acids, peptides, proteins and vitamins); vitamin derivatives (e.g., tocophenyl actetate, niacinamide, panthenol); hair-hold polymers; detersive surfactants (e.g., anionic, nonionic, amphoteric, and zwitterionic surfactants); UV-filters (e.g., p-methoxy cinnamic acid isoamylester, lipophilic cinnamic acid esters, salicylic acid esters, 4-amino benzoic acid derivatives or hydrophilic sulfonic acid derivatives of benzophenones or 3-benzyliden campher); antioxidants (e.g., tocopheroles), preservatives (e.g., benzyl alcohol, methyl paraben, propyl paraben, and imidazolidinyl urea); polyvinyl alcohol; ethyl alcohol; pH-adjusting agents (e.g., citric acid, formic acid, glyoxylic acid, acetic acid, lactic acid, pyruvic acid, sodium citrate, succinic acid, phosphoric acid, sodium hydroxide, and sodium carbonate); salts (e.g., potassium acetate and sodium chloride); antimicrobials; humectants (e.g., sorbitol); chelators (e.g., such as those described in U.S. Pat. No. 5,487,884 issued to Bisset, et al.); sunscreens; desquamation actives (e.g., those described in U.S. Pat. Nos. 5,681,852 and 5,652,228 issued to Bisset); anti-wrinkle/anti-atrophy actives (e.g., N-acetyl derivatives, thiols, hydroxyl acids, phenol); skin soothing agents/skin healing agents (e.g., panthenoic acid derivatives, aloe vera, allantoin); skin lightening agents (e.g., kojic acid, arbutin, ascorbic acid derivatives); skin tanning agents (e.g. dihydroxyacteone); anti-acne medicaments; essential oils; sensates; coloring agents; perfumes; sequestering agents (e.g., disodium ethylenediamine tetra-acetate); and polymer plasticizing agents (e.g., glycerin, disobutyl adipate, butyl stearate, and propylene glycol). Other such suitable examples of such skin actives are described in U.S. Patent Application Publication No. 2012/0009285.

Such optional ingredients generally can be used individually at levels from about 0.01% to about 10.0%, by weight of the liquid foamable composition in certain examples; and in certain examples from about 0.05% to about 5.0% of the liquid foamable composition.

In certain examples, the liquid foamable composition can further include one or more thickening agents to facilitate foam stabilization when the propellant is added to the liquid foamable composition. However, in certain examples, the liquid foamable composition can be substantially free of any thickening agents. Non-limiting classes of thickening agents include those selected from carboxylic acid polymers, cross-linked polyacrylate polymers, polyacrylamide polymers, polysaccharides, and gums. Suitable examples of each are described in U.S. Patent Publication No. 2003/0049212, which is incorporated by reference herein. Additionally, suitable thickening agents can include water-soluble polymers as described in U.S. Pat. No. 8,444,716, which is also incorporated by reference herein. The liquid foamable composition can include from about 0.1% to about 2%, by weight; from about 0.2% to about 1%, by weight; and from about 0.5% to about 1%, by weight, of a polymer thickening agent.

B. Propellant

A variety of conventional propellants (e.g., gases) can be used to transform the liquid foamable composition into a foam composition. Such propellants can include carbon dioxide and nitrous oxide. In certain examples, the propellant can be only one compound, and in other examples, the propellant can be a mixture of compounds. For example, in one example, only carbon dioxide can be used as a propellant. In certain examples, the propellant can include air. Other compounds can also be included to form the propellant in amounts of up to about 1%, by weight of the total propellant. These additional propellant compounds can include propane, butane, isobutane, dimethyl ether, and $N_2O$. These additional propellant compounds can be present without causing any disadvantages. In certain examples, the foam composition can include about 20 parts of propellant per one hundred parts.

In a bag-on-valve system, for example, a propellant can be held within a container, such that the propellant surrounds an inner bag. As described herein, propellants used in a bag-on-valve system can have minimal to no interaction with a liquid foamable composition or a foam composition. As a result, types of propellant that can be used in a bag-on-valve system can be less restrictive than those used in examples where there is more interaction between the propellant and the liquid foamable composition or the foam composition. Suitable propellants for use in a bag-on-valve system can include, for example, hydrocarbons or any of a variety of suitable propellants.

In the foam composition, carbon dioxide can be included at levels of about 0.5% to about 20.0%, by weight, in certain examples; from about 1.0% to about 3.0%, by weight, in certain examples; and from about 1.5% to about 2.5%, by weight, in certain examples.

III. Aerosol Product

An aerosol product can include a liquid foamable composition, a propellant, and a package. In certain examples, the liquid foamable composition and propellant can be housed in the package, which can include a container and a valve, such that the liquid foamable composition and propellant can be combined and dispensed as a foam. In certain examples, a foam composition can be housed in a package.

The container can be any of a variety of aerosol containers or similar type containers known in the art. For example, the container can be a single chamber container or a barrier container. Non-limiting examples of single chamber containers can include plastic, glass, aluminum, or steel containers that can be unlined or lined with materials such as epoxy phenolics, organosols, and polyamide imides. In such single chamber containers, the liquid foamable composition and the propellant can be combined in the single chamber, as shown in FIG. 1. Barrier containers can keep the liquid foamable composition physically separate from the propellant within the container. Non-limiting examples of barrier containers can include a piston container and a bag-on-valve container, which are described in U.S. Patent Publication No. 2012/0288465.

The valve can be any of a variety of aerosol valves or similar type valves (e.g., any of a variety of valves supplied by APTAR®). In certain examples, the valve can be a powder valve. The powder valve can include one or more orifices on a valve stem, normally one or two orifices. Each of the orifices can have a same or different orifice diameter and can be in the form of any of a variety of shapes (e.g., circular, square, etc.). Both the orifice diameter and the orifice shape can be selected based upon the size and shape of the particulate material used in the liquid foamable composition. Further, certain valves, such as a powder valve, can help to prevent clogging of the aerosol product by wiping an opening of the orifice against a sealing gasket as the valve moves from an open position to a closed position. Non-limiting examples of suitable powder valve configurations are described in detail in U.S. Pat. Nos. 3,773,064, 5,975,378, 6,394,321 and 8,580,725.

FIG. 1 shows a portion of a to which a valve is mounted, according to one example. A valve assembly 111 can generally include a dip tube 112, a valve housing 114, a valve-closing coil spring 116, and a valve body 118. The valve body 118 can have a hollow valve stem 120 extending upwardly therefrom and can include at least one orifice 122 leading into an interior of the valve stem 120. A sealing gasket 124, which can be made of rubber or other suitable resilient material, can surround the valve stem 120 and seal the orifice 122 when the valve is in the closed position. An actuator 126 having a nozzle 128 is shown to be attached to a top of the valve stem 120. When the actuator 126 is depressed downwardly against a force of the spring 116, the valve moves to the open position, and the orifice 122 can pass below the sealing gasket 124 such that the liquid foamable composition within the container can, under the influence of the propellant, pass up through the dip tube 112, into the valve body 118, through the orifice 122, into the valve stem 120, into the actuator 126, before being dispensed out through the nozzle 128. When the actuator 126 is released, the valve can return to the closed position, such that the spring 116 can push the valve stem 120 and the orifice 122 upwardly against the sealing gasket 124, wiping any remaining liquid foamable composition away from the orifice 122 of the valve stem 120 to prevent clogging of the orifice 122 and blocking flow of the liquid foamable composition.

The actuator 126 can be any of a variety of actuators known in the art. For example, an actuator can be a front-hinged, rear-hinged, or non-hinged actuator, as long as the actuator can be properly matched with the valve stem. Non-limiting examples of suitable hinged actuators can include those available from SEAQUIST® Perfect Dispensing under the trade names S30, S25, S20, and Allegra for upright containers and S16 and S4 for inverted containers. Non-hinged actuators can be used as they can tend to exhibit less lateral pressure during actuation of the aerosol product. Non-limiting examples of suitable non-hinged actuators can include those available from Precision Valve under the trade names City Spout, Hercules Spout, and Iris and those available from SEAQUIST® Perfect Dispensing under the trade name S2. Actuators, valves, containers, and other related parts and equipment can include those available from, for example, APTAR®, Precision Valve, and Summit Packaging Systems.

Figure 2:
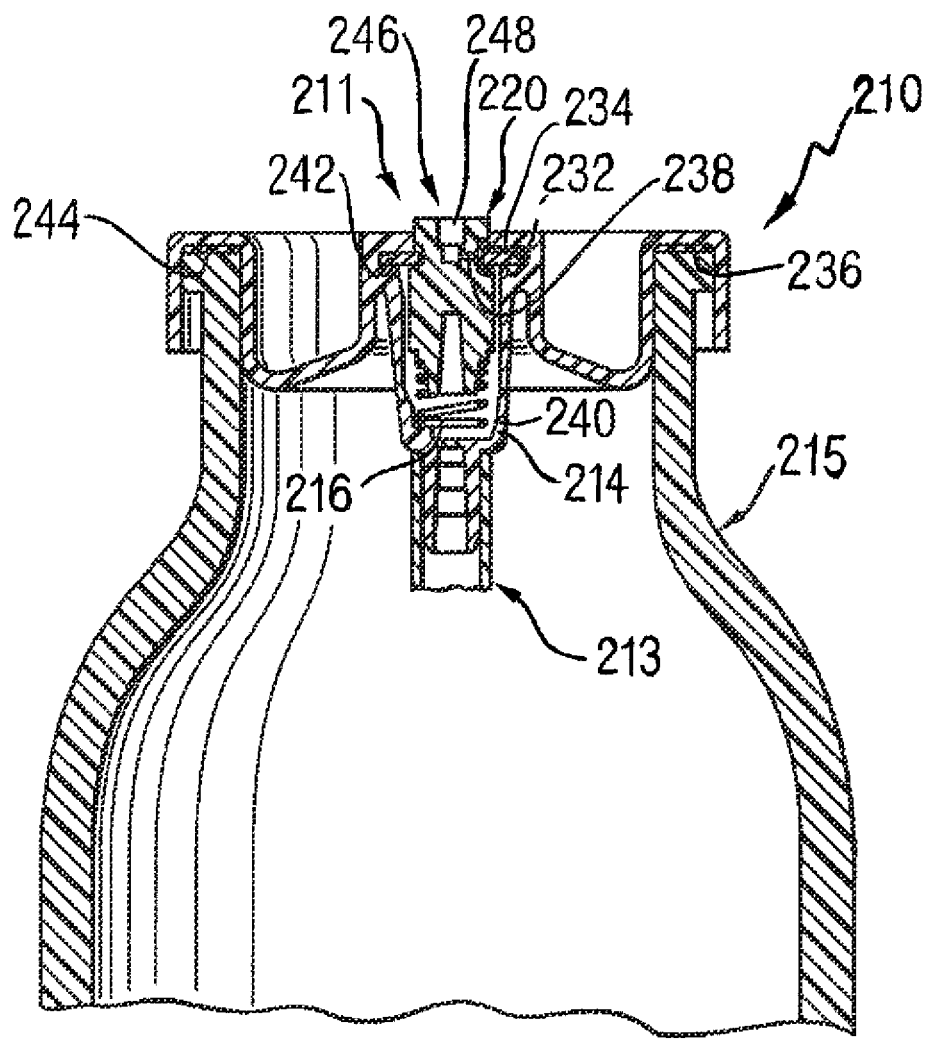
FIG. 2 depicts a schematic cross-sectional view of an inner bag housed within a container according to another example.
Figure 3:
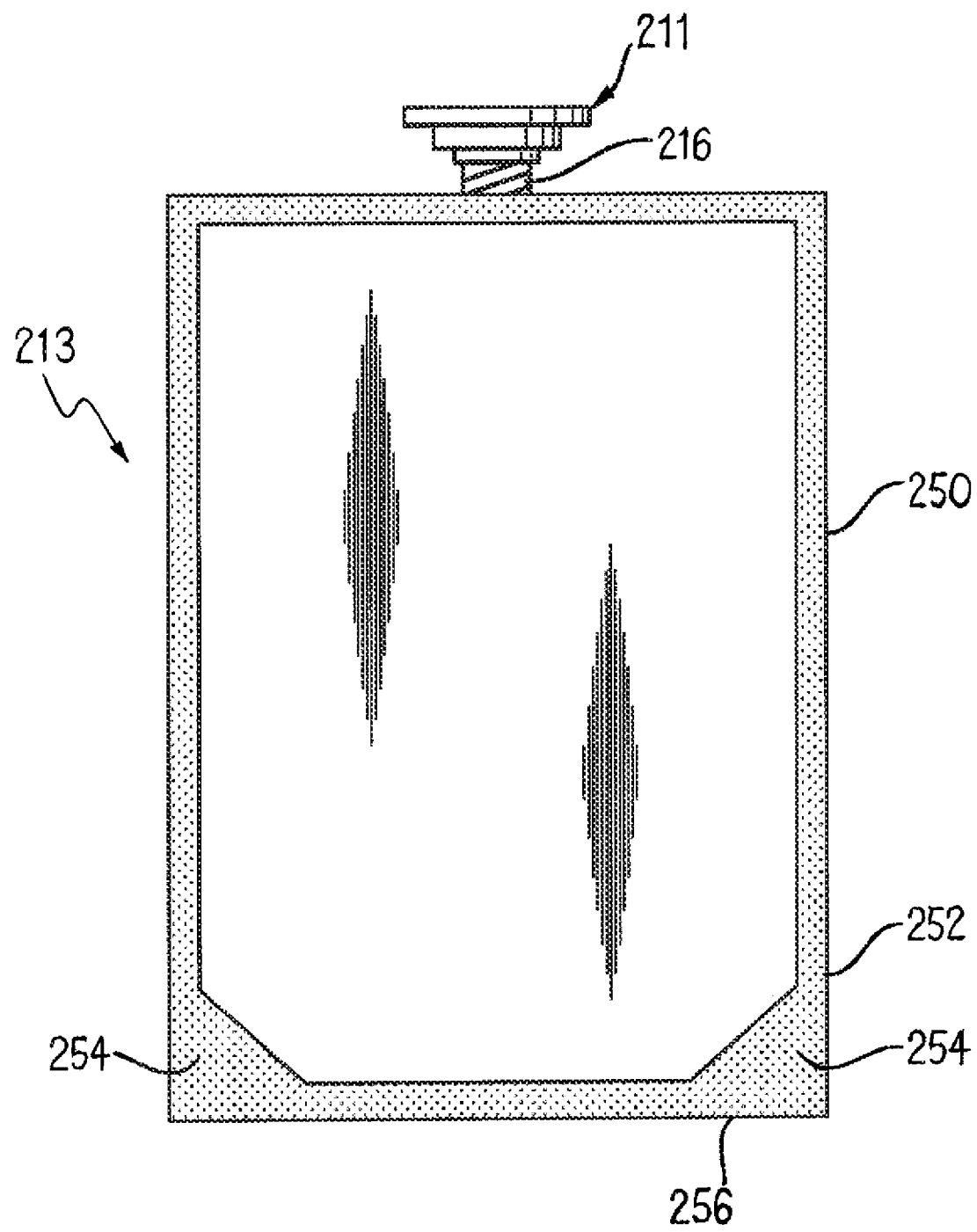
FIG. 3 depicts a front view of the inner bag of FIG. 2.

In another example, a container can include a bag-on-valve system, as mentioned herein and as shown in FIGS. 2 and 3. FIG. 2, for example, shows a bag-on-valve system including a container 210 having an inner bag 213, which can be filled with the foam composition or the liquid foamable composition, and an outer container 215, which can enclose the inner bag 213. A valve assembly 211, vertically movable between an open position and a closed position, can be attached to the inner bag 213.

The valve assembly 211 can include a housing 214, a valve stem 220, a spring 216, a valve plate 232, an inner sealing 234, and an outer sealing 236. The valve stem 220 can include one or more lateral openings 238. The spring 216 can be disposed between a lower end portion 240 of the valve stem 220 and the housing 214 and can bias the valve stem 220 upwardly towards the valve plate 232, which can be disposed at an upper end of the housing 214. The valve plate 232 can include two coaxially-arranged recesses 242, 244 extending in a circumferential direction of the valve plate 32. FIG. 2 shows an axial opening 246 located in a central portion of the inner recess 242. The inner sealing 234 can be disposed within the inner recess 242, attached to the valve plate 232, and can be adapted to engage the valve stem 220 such that the lateral opening 238 of the valve stem 220 is covered and blocked, respectively. The outer sealing 236 can be disposed in the second or outer recess 244 of the valve plate 232. The valve stem 220 can include a passage 248 in the central axial portion thereof, which can be connected to the lateral opening 238 on one side and connectable to a corresponding passage of a dispenser cap on the other side. In the closed position, a flow path from the interior space of the housing 214 along the valve stem 220 and through the lateral opening 238 can be blocked by the inner sealing 234.

The valve assembly 211 can be fixed to the inner bag 213 at an upper end thereof such that a lower end of the housing 214 of the valve assembly 211 can be gas-tight covered by the upper edge of the inner bag 213. Further, the inner bag 213 and the valve assembly 211 can be attached to the outer container 215 such that an upper end of the outer container 215 can engage the outer sealing 236 of the valve plate 232 in a gas-tight manner. Accordingly, an interior of the inner bag 213 and space between the outer container 215 and the inner bag 213 each can be independently sealed.

A dispenser cap having an actuator (not shown) can be attached to the valve plate 232 such that the actuator can engage the valve stem 220. When the actuator is depressed downwardly against a force of the spring 216, the valve assembly 211 can move to the open position. The valve stem 220 moves within the inner sealing 234, which can remain stationary, while contacting the same. Once the lateral opening 238 can be uncovered by the inner sealing 234, the flow path from the valve housing 214 through the lateral opening 238 can be opened. Thus, the interior of the inner bag 213 and the flow path inside the valve housing 214 become linked such that the foam composition/liquid foamable composition within the inner bag 213 can pass through the flow path and dispensed out of the dispenser cap by the pressure of the propellant/compressed gas, which can surround the inner bag 213.

As shown in FIG. 3, the inner bag 213 can include flat lateral edges 250 and a bottom fold 252, which can be directed towards an upper end of the inner bag 213 in order to allow a controlled collapse. Near the bottom fold 252, the inner bag 213 can include two flat triangular portions 254, each extending from the bottom edge 256 to the lateral edge 250 with an angle of about 45°. This can further facilitate the collapse of the inner bag 213, when compressed by the pressure of the propellant in the outer container 215 (as shown in FIG. 2). As described above, the outer container 215 can include any of a variety of propellants or any other suitable compressed gas. Pressure of the propellant can be set to from about 0.3 to about 1.0 MPa, or from about 0.3 to about 0.8 MPa, in order to stably discharge contents of the inner bag 213 as completely as possible.

The inner bag can be flexible, and can be made from any of a variety of suitable materials. In certain examples, the inner bag can be formed with a layer of a material that can be essentially impermeable to the propellant within the inner bag. In certain examples, the inner bag can be formed with a layer of a material that can be essentially impermeable to the propellant outside of the bag, as it may be required that such compositions do not mix during storage. Mixing of the propellant within the inner bag and the propellant outside of the bag can be inappropriate based on the properties of the foam composition/liquid foamable composition or any of a variety of other reasons. However, this does not preclude the possibility that the propellant within the inner bag and the propellant outside of the bag can be mixed upon dispensing of the foam composition/liquid foamable composition when a valve to dispense the foam is triggered. For example, a mixing channel (not shown) or another appropriate measure can be used in such a case to mix the respective propellants if desired.

IV. Method of Use

The foam composition can be used in conventional ways to improve sensory benefits to skin. This generally involves application of an effective amount of the foam composition to a portion of the skin of a user. For example, the foam composition can be dispensed from an aerosol can or similar container or package, and the foam composition can be applied and rubbed onto a desired portion of the skin of a user. An "effective amount" can refer to an amount sufficient enough to provide the desired sensory benefits, which can include, for example, a rich and creamy appearance and a favorable "feel."

In certain embodiments, the foam composition can provide the rich and creamy appearance and moisturization and protection capabilities associated with heavier products, while providing a rapid absorption and ease of application associated with lighter products. Furthermore, the foam composition can reduce or eliminate characteristics associated with a negative sensory experience such as, for example, tack, drag, and stickiness.

V. Procedures

A. Foam Density Determination

From a pressurized dispenser containing the foam composition, dispense enough foam into a small cylindrical cup-like container of known volume (or dimensions) and weight, such that the foam composition can rise above a rim of the cup-like container. Using a tool with a straight edge, such as a spatula, scrape off any excess foam by sweeping an edge of the spatula across the rim of the cup-like container to leave a flat smooth surface at level with a top of the cup-like container. Weigh the foam composition and the container, and calculate a foam density using the following formula:

$$\text{foam density} = \frac{\text{weight of cup with foam (g)} - \text{weight of empty cup (g)}}{\text{Volume of Cup (mL)}}$$

Assuming the cup-like container is cylindrical, the volume of the container can be calculated by measuring its diameter and depth with, for example, a caliper or similar measuring tool. The volume can then be calculated using the following formula:

$$\text{Volume} = (\pi) \times (\text{cup height [mm]}) \times \left(\frac{\text{cup diameter [mm]}}{2}\right)^2$$

VI. Examples

A. Inventive Example

Table 1 shows formulas for inventive examples of the liquid foamable composition.

TABLE 1

Inventive Examples A-E of Liquid Foamable Compositions

| Ingredient | Amount (wt. %) | | | | |
|---|---|---|---|---|---|
| | Inventive Ex. A | Inventive Ex. B | Inventive Ex. C | Inventive Ex. D | Inventive Ex. E |
| Cyclopentasiloxane | 3.8 | 3.6 | 3.6 | 3.5 | 3.2 |
| Silicone Gel 1[1] | 11.8 | 8.1 | 8.0 | 7.5 | 7.0 |
| Silicone Gel 2[2] | — | 3.2 | 3.2 | 3.0 | 2.5 |
| Silicone Powder 1[3] | 3.2 | 2.9 | 3.3 | — | 3.3 |
| Silicone Powder 2[4] | — | 1.5 | 3.1 | 1.5 | 3.1 |
| Silicone Powder 3[5] | — | — | — | 2.5 | — |
| Silicone Powder 4[6] | 1.6 | — | — | 0.5 | — |
| Wetting Agent[7] | 0.6 | 0.5 | 0.4 | — | 0.4 |
| Cetyl Alcohol | 1.0 | 0.9 | 0.9 | 0.9 | 1.1 |
| Stearyl Alcohol | 2.0 | 2.3 | 2.3 | 2.3 | 2.5 |
| Behenyl Alcohol | 0.5 | — | — | — | — |
| Behenyl Trimethyl Ammonium Chloride | 1.5 | 1.4 | 1.3 | 1.4 | 1.6 |
| Glycerin | 3.0 | — | — | 5.0 | — |
| Superabsorbent Polymer[8] | — | — | — | 0.25 | — |
| Water | Q.S. | Q.S. | Q.S. | Q.S. | Q.S. |
| Propellant | $N_2O$ | $N_2O$ | $CO_2$ | $CO_2$ | $CO_2$ |

[1]DC 9040: Cyclopentasiloxane (and) Dimethicone Crosspolymer, Dow Corning Corp.
[2]KSG-16: Dimethicone (and) Dimethicone/Vinyl Dimethicone Crosspolymer, Shin-Etsu Corp.
[3]DC 9506: Dimethicone/Vinyl Dimethicone Crosspolymer, Dow Corning Corp.
[4]KSP-105: Vinyl Dimethicone/Methicone Silsesquioxane Crosspolymer, Shin-Etsu Corp.
[5]KSP-102: Vinyl Dimethicone/Methicone Silsesquioxane Crosspolymer, Shin-Etsu Corp.
[6]Tospearl 120A: Polymethylsilsesquioxane, Momentive Corp.
[7]SF 1288: PEG-12 Dimethicone, Momentive Corp.
[8]Sodium Polyacrylate Starch Each of the inventive examples can be prepared by combining the water, cationic surfactant, and fatty alcohol and heating the mixture to about 80° C. Liquid crystal structures (e.g., a lamellar gel structure) can be formed as the quaternary ammonium compound and the fatty alcohol combine to emulsify, stabilize, and thicken the water phase. The mixture can then be allowed to cool. Subsequently, the remaining components can be added to the cooled lamellar gel. Each of Inventive examples A-D and Comparative Examples A-C, which are listed below, was dispensed from a conventional aerosol-type can. Inventive Example E was incorporated into a bag-on-valve system for dispensing. As shown above, Inventive Examples A and B used $N_2O$ as a propellant, while Inventive Examples C-E used $CO_2$. Each of Comparative Examples A-C employed isobutane and propane as the propellant.

TABLE 2

Foam Density Measurements

| Examples | Foam Density (g/mL) |
| --- | --- |
| Comparative Example A (OLAY ® Definity Deep Penetrating Foaming Moisturizer) | 0.066 |
| Comparative Example B (OLAY ® Regenerist Reversal Treatment Foam) | 0.064 |
| Comparative Example C (SHU UEMURA ® Whiteffieient UV Under Base Brightening Mousse) | 0.089 |
| Inventive Example A | 0.126 |
| Inventive Example B | 0.133 |
| Inventive Example C | 0.144 |
| Inventive Example D | 0.144 |
| Inventive Example E | 0.210 |

As described above, Table 2 shows inventive examples of a foam composition (i.e., Inventive Examples A-E) outperforming comparative examples (i.e., Comparative Examples A-C) with respect to foam density. As foam density of a foam composition increases, the foam composition can become stiffer, and thus can offer a thicker, richer foam to the touch of a user. Further examples according to the present invention are given in table 3, below.

TABLE 3

| | BTMS level Inventive Example 1 | BTMS level Inventive Example 2 | BTMS level Inventive Example 3 | Cat + Non Inventive Example 4 |
| --- | --- | --- | --- | --- |
| BTMS (behentrimonium methosulfate) | 0.05 | 0.1 | 0.2 | 0.25 |
| PEG 100 Stearate | x | x | x | 0.075 |
| Emulgade P 68/50 | x | x | x | 0.15 |
| Cetyl Alcohol | 1.8 | 0.65 | 0.65 | 1.15 |
| Stearyl Alcohol | 4.5 | 1.1 | 1.1 | 0.46 |
| Behenyl Alcohol | 1 | 0.95 | 0.95 | x |
| KF6011 P | 0.5 | 0.25 | 0.25 | 0.25 |
| Glycerin | 5 | 2.5 | 2.5 | x |
| Silicone elastomer (DC 9045) | 8 | 4 | 4 | 4.125 |
| Silicone fluid (Cyclopentasiloxane) | 4 | 2 | 2 | 1.875 |
| Silicone Gum (KSG 16) | 3.5 | 1.75 | 1.75 | 1.65 |
| Silicone Powder 1 (KSP 105) | 1 | 0.6 | 0.5 | 0.75 |
| Silicone Powder 2 (Tospearl 145A) | 3.5 | 2.5 | 2.5 | x |
| Silicone Powder 3 (DC 9701) | x | x | x | 1.6 |
| Water | q.s. | q.s. | q.s. | q.s. |
| Propellant | Nitrous Oxide | Nitrous Oxide | Nitrous Oxide | Nitrous Oxide |
| Wt. of foam | 18.35 | 18.87 | 19.24 | 19.89 |
| Volume of Container (r = 2.5 cm, h = 5 cm) | 98.175 | 98.175 | 98.175 | 98.175 |
| Density (g/ml) | 0.1869 | 0.1922 | 0.1960 | 0.2026 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The products and methods/processes of the present disclosure can comprise, consist of, and consist essentially of the essential elements and limitations of the invention described herein, as well as any of the additional or optional ingredients, components, steps, or limitations described herein.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in the document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid foamable composition for preparing a foam having a density from 0.12 g/mL to about 0.5 g/mL comprising:
   from about 0.05% to about 5% by weight, of a cationic surfactant and mixtures thereof with nonionic surfactants;
   from about 1% to about 10% by weight, of a fatty alcohol;
   from about 10% to about 50% by weight, of a silicone blend, the silicone blend comprising:
   a first silicone component comprising a silicone gel selected from dimethicone/vinyl dimethicone crosspolymer and a mixture of dimethicone and dimethicone/vinyl dimethicone crosspolymer; and
   a second silicone component comprising a silicone powder: and
   from about 50% to about 80%, by weight, of water;
   wherein the silicone blend comprises:
   from about 75% to about 85%, by weight, of the first silicone component; and from about 15% to about 25%, by weight, of the second silicone component.

2. The liquid foamable composition of claim 1, comprising from about 12% to about 30%, by weight, of the silicone blend.

3. The liquid foamable composition of claim 1, wherein each of the first silicone component and the second silicone component are crosslinked silicone elastomers.

4. The liquid foamable composition of claim 1, wherein the ratio of the first silicone component to the second silicone component is about 3 parts to about 1 part.

5. The liquid foamable composition of claim 1, wherein the silicone blend further comprises from about 0.05% to about 4%, by weight, of a wetting agent.

6. The liquid foamable composition of claim 1, wherein the surfactant and the fatty alcohol combine to form liquid crystal structures, wherein the liquid crystal structures are of a phase selected from the group consisting of bicontinuous cubic, hexagonal, inverse cubic, lamellar gel, micellar cubic, reverse hexagonal columnar, and combinations thereof.

7. The liquid foamable composition of claim 6, wherein the liquid crystal structures are of a lamellar gel phase.

8. The liquid foamable composition of claim 6, wherein the liquid foamable composition is substantially free of a thickening agent.

9. The liquid foamable composition of claim 1 comprising from about 0.05% to about 4%, by weight, of the surfactant.

10. The liquid foamable composition of claim 1, wherein the fatty alcohol has a melting point of about 25° C. or higher.

11. The liquid foamable composition of claim 10, wherein the fatty alcohol comprises one or more of behenyl alcohol, cetyl alcohol, and stearyl alcohol.

12. The liquid foamable composition of claim 1, wherein the cationic surfactant comprises a quaternary ammonium compound.

13. The liquid foamable composition of claim 12, wherein the quaternary ammonium compound comprises one or more of behenyl trimethyl ammonium chloride, stearamidopropyl dimethylamine, behentrimonium methosulfate, behenylamidopropyl dimethylamine, stearyl ethylhexyldimonium methosulfate, dicetyldimonium chloride, and ditallow dimethyl ammonium chloride.

14. The liquid foamable composition of claim 1, further comprising a superabsorbent polymer.

15. The liquid foamable composition of claim 1, further comprising an active compound, the active compound comprising one or more of niacinamide, panthenol, and hexyldecanol.

16. A foam composition formed from combining a liquid foamable composition according to claim 1 with a propellant and
wherein the foam composition exhibits a foam density from 0.12 g/mL to about 0.5 g/mL; and
wherein the silicone blend further comprises from about 0.05% to about 4%, by weight, of a wetting agent.

17. The foam composition of claim 16, exhibiting a foam density of 0.12 g/mL to about 0.4 g/mL.

18. The foam composition of claim 16, wherein the propellant comprises carbon dioxide.

19. The foam composition of claim 16, wherein the surfactant and the fatty alcohol combine to form liquid crystal structures, wherein the liquid crystal structures are of a phase selected from the group consisting of bicontinuous cubic, hexagonal, inverse cubic, lamellar gel, micellar cubic, reverse hexagonal columnar, and combinations thereof.

20. The foam composition of claim 19, wherein the liquid crystal structures are of a lamellar gel phase.

21. The foam composition of claim 19, wherein the foam composition is substantially free of a thickening agent.

22. The foam composition of claim 16, wherein the liquid foamable composition comprises from about 0.5% to about 4%, by weight, of the surfactant.

23. The foam composition of claim 16, wherein the cationic surfactant comprises a quaternary ammonium compound.

24. The foam composition of claim 23, wherein the quaternary ammonium compound comprises one or more of behenyl trimethyl ammonium chloride, stearamidopropyl dimethylamine, behentrimonium methosulfate, behenylamidopropyl dimethylamine, stearyl ethylhexyldimonium methosulfate, dicetyldimonium chloride, and ditallow dimethyl ammonium chloride.

25. The foam composition of claim 16, wherein the liquid foamable composition further comprises a superabsorbent polymer.

26. The foam composition of claim 16 is configured to be dispensed from an aerosol package.

27. An aerosol product comprising:
a liquid foamable composition according to claim 1
a propellant; and
a package housing the liquid foamable composition and a propellant; and
wherein the liquid foamable composition and the propellant are dispensable from the package as a foam, wherein such foam exhibits a foam density of from 0.12 g/mL to about 0.5 g/mL.

28. The aerosol product of claim 27, wherein the propellant comprises carbon dioxide.

29. The aerosol product of claim 27, wherein the cationic surfactant comprises a quaternary ammonium compound, wherein the quaternary ammonium compound comprises one or more of behenyl trimethyl ammonium chloride, stearamidopropyl dimethylamine, behentrimonium methosulfate, behenylamidopropyl dimethylamine, stearyl ethylhexyldimonium methosulfate, dicetyldimonium chloride, and ditallow dimethyl ammonium chloride.

30. A method for improving sensory benefits to skin comprising:
applying a foam composition according to claim 16 to the skin of a user.

31. The method of claim 30, wherein prior to applying the foam composition, a user dispenses the foam composition from an aerosol package.

32. The method of claim 16, wherein the foam composition exhibits a foam density of about 0.12 g/mL to about 0.4 g/mL.

33. The method of claim 30, wherein the cationic surfactant comprises a quaternary ammonium compound, wherein the quaternary ammonium compound comprises one or more of behenyl trimethyl ammonium chloride, stearamidopropyl dimethylamine, behentrimonium methosulfate, behenylamidopropyl dimethylamine, stearyl ethylhexyldimonium methosulfate, dicetyldimonium chloride, and ditallow dimethyl ammonium chloride.

34. The method of claim 33, wherein the surfactant and the fatty alcohol combine to form liquid crystal structures, wherein the liquid crystal structures are of a phase selected from the group consisting of bicontinuous cubic, hexagonal, inverse cubic, lamellar gel, micellar cubic, reverse hexagonal columnar, and combinations thereof.

* * * * *